(12) United States Patent
Pazderski et al.

(10) Patent No.: US 12,260,850 B2
(45) Date of Patent: Mar. 25, 2025

(54) BRAIN COMPUTER INTERFACE RUNNING A TRAINED ASSOCIATIVE MODEL APPLYING MULTIWAY REGRESSION TO SIMULATE ELECTROCORTICOGRAPHY SIGNAL FEATURES FROM SENSED EEG SIGNALS, AND CORRESPONDING METHOD

(71) Applicant: MINDSPELLER BCI BV, Leuven (BE)

(72) Inventors: Pawel Piotr Pazderski, Leuven (BE); Hannes Flora Jan De Wachter, Herent (BE)

(73) Assignee: MINDSPELLER BCI BV, Leuven (BE)

( * ) Notice: Subject to any disclaimer, the term of this patent is extended or adjusted under 35 U.S.C. 154(b) by 328 days.

(21) Appl. No.: 17/788,566

(22) PCT Filed: Dec. 18, 2020

(86) PCT No.: PCT/EP2020/087040
§ 371 (c)(1),
(2) Date: Jun. 23, 2022

(87) PCT Pub. No.: WO2021/130115
PCT Pub. Date: Jul. 1, 2021

(65) Prior Publication Data
US 2023/0025518 A1   Jan. 26, 2023

(30) Foreign Application Priority Data
Dec. 24, 2019   (NL) ..................................... 2024573

(51) Int. Cl.
*G10L 13/027*   (2013.01)
*G06F 3/01*     (2006.01)
*G10L 13/04*    (2013.01)

(52) U.S. Cl.
CPC ............ *G10L 13/027* (2013.01); *G06F 3/015* (2013.01); *G10L 13/04* (2013.01)

(58) Field of Classification Search
CPC . G06F 3/00; G06F 3/015; G10L 13/00; G10L 13/04; G10L 13/027
See application file for complete search history.

(56) References Cited

U.S. PATENT DOCUMENTS 10,856,815 B2 *  12/2020  Pereira ...................... G06N 3/08
2013/0165812 A1 *  6/2013  Aksenova .............. A61B 5/375
                                                           600/544

(Continued)

FOREIGN PATENT DOCUMENTS

CN       107569228 A     1/2018
WO      2021/130115 A1   7/2021

OTHER PUBLICATIONS

ISR-WO dated Feb. 10, 2021 for parent application PCT/EP2020/087040.

(Continued)

*Primary Examiner* — Daniel C Washburn
*Assistant Examiner* — Sean E Serraguard
(74) *Attorney, Agent, or Firm* — Vorys, Sater, Seymour and Pease, LLP

(57) ABSTRACT

Brain computer interface BCI comprising an input adapted to be connected to at least one electroencephalography EEG sensor to receive EEG signals, the BCI further comprising a processor running an associative model trained to simulate electrocorticography ECoG signal features from EEG signals received via the input, the BCI comprising an output to transmit the simulated ECoG signal features.

12 Claims, 6 Drawing Sheets

(56) References Cited

U.S. PATENT DOCUMENTS

| | | | |
|---|---|---|---|
| 2016/0282941 A1* | 9/2016 | Aksenova | A61B 5/7203 |
| 2019/0212816 A1* | 7/2019 | Myrden | A61B 5/378 |
| 2020/0229730 A1* | 7/2020 | Wang | A61B 5/7278 |
| 2022/0215955 A1* | 7/2022 | Sajda | G06T 9/002 |

OTHER PUBLICATIONS

Camarrone Flavio et al, "Fast Multiway Partial Least Squares Regression", Feb. 1, 2019 (Feb. 1, 2019), vol. 66, No. 2, p. 433-443.
Fifer Matthew S et al, "Design and implementation of a human ECoG simulator for testing brain-machine Interfaces", Nov. 6, 2013 (Nov. 6, 2013), p. 1311-1314.
Krusienski D J et al, "A case study on the relation between electroencephalographic and electrocorticographic event-related potentials", 2010 Annual International Conference of the IEEE Engineering in Medicine and Biology Society : (EMBC 2010) ; Buenos Aires, Argentina, Aug. 31-Sep. 4, 2010, IEEE, Piscataway, NJ, USA, Aug. 31, 2010 (Aug. 31, 2010), p. 6019-6022.
Anderson N R et al, "An Offline Evaluation of the Autoregressive Spectrum for Electrocorticography", IEEE Transactions On Biomedical Engineering, IEEE Service Center, Piscataway, NJ, USA, vol. 56, No. 3, Mar. 1, 2009 (Mar. 1, 2009), p. 913-916.
Anh Huy Phan et al, "A tensorial approach to single trial recognition for Brain Computer Interface", Advanced Technologies for Communications (ATC), 2010 International Conference On, IEEE, Piscataway, NJ, USA, Oct. 20, 2010 (Oct. 20, 2010), p. 138-141.

\* cited by examiner

FIG. 4

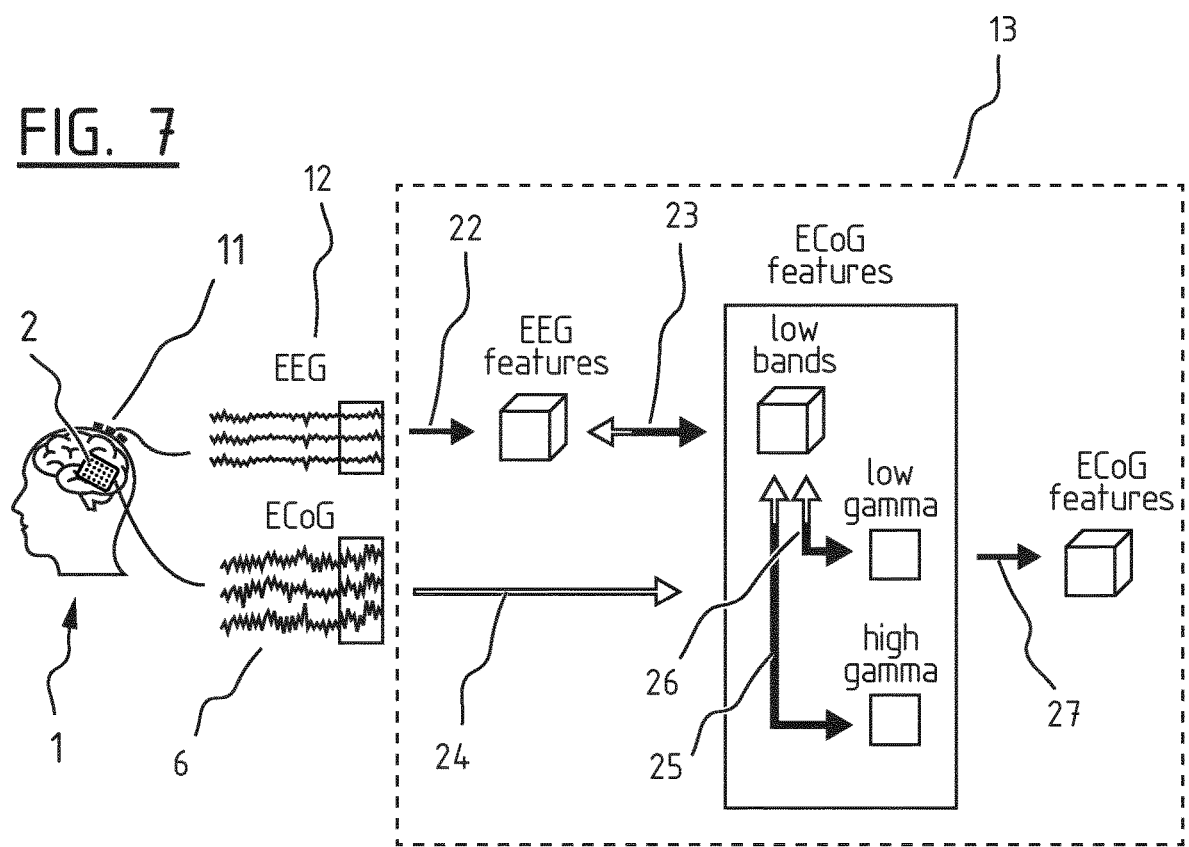

BRAIN COMPUTER INTERFACE RUNNING A TRAINED ASSOCIATIVE MODEL APPLYING MULTIWAY REGRESSION TO SIMULATE ELECTROCORTICOGRAPHY SIGNAL FEATURES FROM SENSED EEG SIGNALS, AND CORRESPONDING METHOD

The present invention relates to a brain computer interface BCI. In particular, the invention relates to mind reading techniques encoded in a speech BCI.

Mind reading techniques are developed for multiple purposes and applications. A first application aims at marketers in search of unveiling customer's thoughts for example relating to brand perceptions, buying preferences and commercial messages. In other applications, engineers aim to supply patients unable to communicate with alternative communication channels. In yet other applications, visionaries seek to develop new ways to interact with technology. For each of these applications and aims, it is a goal to be able to synthesize speech, for example word- and sentence-level communication, to express emotional state, for example anger, sadness, fear, happiness, and disgust, clause type, for example statement, question, command, and exclamation, as well as gestures and other forms of physical activity from brain activity.

Electrocorticography ECoG, or intracranial electroencephalography iEEG, is a type of electrophysiological monitoring, the output of which is in this description referred to as ECoG recordings, that uses electrodes placed directly on the exposed surface of the brain to record electrical activity from the cerebral cortex. Such ECoG recording is not exactly 'neural' in the sense of activity of individual neurons or nerve cells, but is related to activity from a large neural population, and is therefore sometimes referred to as neural recordings. ECoG may be performed either in the operating room during surgery, referred to as intraoperative ECoG, or outside of surgery, referred to as extraoperative ECoG. Because a craniotomy, being a surgical incision into the skull, is required to implant the electrode grid, ECoG is an invasive procedure.

In recent years, electrocorticography ECoG has gained considerable ground in speech BCI research owing to its superior spatial and temporal resolution capturing the fast-changing dynamics of brain regions involved in speech processing. This is described in "Progress in speech decoding from the electrocorticogram" by Chakrabarti et al., published in Biomedical Engineering Letters in 2015. In prior art publications, both 'discrete' approaches, words, vowels, phonemes, . . . and 'continuous' approaches, spectrograms, vocoder representations, . . . are described to synthesize textual representations and audible speech, respectively, from ECoG recordings. A drawback is that ECoG implants primarily serve a clinical purpose and recording techniques that do not require craniotomies are almost by definition preferred when commercial applications are envisaged.

It is an object of the present invention to develop mind reading techniques wherein a craniotomy can be avoided.

To this end, the invention proposes a brain computer interface BCI comprising an input adapted to be connected to at least one electroencephalography EEG sensor to receive EEG signals, the BCI further comprising a processor running an associative model applying a multiway regression approach trained to simulate electrocorticography ECoG signal features from EEG signals received via the input, the BCI comprising an output to transmit the simulated ECoG signal features.

In contrast to ECoG, conventional electroencephalography EEG records electrophysiological activity from electrodes placed on the scalp. Therefore EEG is preferred over ECoG particularly in commercial applications. However, current developments of mind reading techniques focus on ECoG and particularly uniquely rely on gamma band activity. Compared to ECoG, EEG has a significantly more limited frequency band and gamma band is usually not recorded because in EEG recordings gamma band is prone to noise and muscular artifacts. A multiway or tensor-based regression approach accounts better than conventional vector- or matrix-based techniques for ECoG signals being structured at least in frequency, space, linked to the position of the electrodes, and time.

The invention is based on the insight that high-gamma band activity is at least to a large extent reflected by broadband modulations in EEG recordings. An example of a particular insight relating to ECoG signals is that performed speech, perceived speech and inner speech share high-gamma activity in a range of 70-150 Hz in the perisylvian cortex. These shared high-gamma activities are to a large extent reflected in lower frequency bands. ECoG signal features are therefore predictable from EEG recordings. Using this knowledge, an associative model is built and trained to simulate ECoG signal features from EEG recordings. The simulated ECoG signal features are predicted from the EEG signals and are therefore related thereto. The BCI with the abovementioned features enables to record signals via EEG, not requiring a craniotomy, and transform these signals in ECoG signals or signal features. This approach enables to maximally reuse the models developed for ECoG recordings, but now for EEG recordings. These ECoG-based speech decoders can be used downstream of the BCI of the invention, connected to the output of the BCI, to decode speech from simulated ECoG signal features.

Preferably, the processor running the associative model is configured to operate in two stages, wherein
  in a first stage features in a first frequency band of the ECoG signal are simulated based on the EEG signals, wherein the first frequency band corresponds to the EEG signal frequency band;
  in a second stage features in a higher frequency band of the ECoG signal are simulated based on the EEG signals.

Tests and simulations have shown that signal features from ECoG can be derived relatively easy from EEG signals in a frequency band that corresponds to the frequency band of EEG. It has further been observed that ECoG signal predictability across frequency bands reflect broadband modulations in human brain activity. Therefore higher frequency signal features can be simulated based on the EEG signals. It will be clear that the high frequency signal features can be simulated directly or indirectly based on the EEG signals. When the high frequency signal features are indirectly based on the EEG signals, they may be based on the simulated ECoG signal features in the first frequency band of the ECoG signal.

Preferably, the first frequency band comprises frequencies below the gamma band. The higher frequency band comprises a low gamma band and a high gamma band and wherein processor is further configured, in the second stage, to separately perform feature simulation in a low gamma band and in a high gamma band.

It has been observed during tests that the prediction of low gamma—(40-70 Hz) from lower frequency band non-task related activity allows to achieve prediction accuracies up to 90%, according to the Pearson correlation coefficient, an example of which is described hereunder, which provides evidence for a substantial degree of low gamma predictability. The prediction accuracies decrease towards the high gamma band such that it is advantageous to separately perform simulation for low and high gamma band signal features.

Preferably, the processor running the associative model comprises a training state and an operational state, wherein at least in the training state, the BCI comprises a further input adapted to be connected to at least one ECoG sensor to receive ECoG signals such that via the input and the further input, EEG signals and ECoG signals can be simultaneously received, and wherein the processor is adapted to train the associative model by feeding the model with the simultaneously received EEG and ECoG signals.

The invention is based on the insight that the associative model can be trained by feeding the model with simultaneously recorded EEG and ECoG signals. Such model is able to perform a prediction of ECoG signal features based on EEG signal features, extracted from EEG recordings in a sliding window. Benefitting from joint scalp—and intracranial EEG recordings, a unique position is achieved to directly tap into the brain areas involved in the perception, production and imagination of speech, learn which signal features can be picked up at scalp level and used, independently from intracranial recordings, to achieve continuous speech or discrete word- and sentence-level communication. In theory, different mathematical models can be used, for example deep learning models or linear learning models.

Preferably the training state comprises three training stages, a first training stage relating to perceived speech, a second training stage relating to performed speech, a third training stage relating to inner speech, signals being fed into the model at least for each of these stages separately.

It has been observed that neural activities partially overlap for different speech paradigms. Current models predominantly focus on either listening, performing or imagining speech, whereas decoder training would significantly benefit from combining speech paradigms because the neural activities partially overlap. In the context of this invention, separately feeding signals into the model for each of these stages is not limited to individually feeding signals into the model for each stage. Signals of two stages could be combined and fed into the model, so that the third stage is also separated from the signals. While separately feeding the signals into the model for each of the stages or combinations of the stages, metadata indicating the stage or stages relevant to the signals is also fed into the model. This allows the model to learn to predict different types of speech.

Preferably, the associative model comprises a block term tensor regression BTTR scheme. Recently, a multiway algorithm was developed called Block Term Tensor Regression BTTR. A key feature of BTTR is that it automatically selects the optimal model parameters. Given the promising performances BTTR is used to predict low gamma signal amplitudes from lower frequency band amplitudes. Tests have shown that the time necessary to train the BTTR model is significantly shorter than training deep learning models such as a deep neural network. BTTR can be used to analyze signals and to extract signal features from the signals. These signal features represent the signal at least in terms of the relevant information that is to be retrieved from the signal. In this description, the term signal features is used to indicate the information derived from a signal, which information represents the signal and represents relevant information from the signal.

It is noted that other multiway regression approaches may be applied instead of the BTTR. A first valid alternative to BTTR is Higher-Order Partial Least Squares HOPLS, published by Zhao et al. in 2013, titled: Higher-Order Partial Least Squares (HOPLS): A Generalized Multi-Linear Regression Method, incorporated herein by reference for explaining the HOPLS multiway regression modeling. In this context it is noted that a limitation of HOPLS is the assumed prior knowledge of the model parameters. When that information is lacking, HOPLS needs to resort to computationally expensive techniques such as cross-validation to identify the optimal set of model parameters, i.e., the number of scores and loadings. In contrast, BTTR automatically determines the model parameters, i.e., the number of loadings, leading to a model that combines high flexibility with a more natural representation of complex multiway data, although it still requires a rather simple cross-validation to determine the number of scores, so-called blocks.

A second valid alternative regression model is pruning sparse Tucker decomposition PSTD, published by Yokota and Cichocki in 2014, titled "Multilinear tensor rank estimation via Sparse Tucker Decomposition", incorporated by reference for explaining the PSTD. The PSTD objective is to minimize the L1-norm of the core tensor under conditions of error bound and orthogonality constraints of individual basis matrices.

A third valid alternative regression model is automatic relevance determination ARD Tucker, published by Mørup and Hansen in 2009, titled: Sparse Coding and Automatic Relevance Determination for Multi-way models, incorporated by reference for explaining the ARD Tucker. The ARD Tucker proposes a method based on Bayesian learning for sparse Tucker decomposition. In this method, the core tensor and matrices are alternately and iteratively updated, while the number of components in each mode are determined using ARD.

A fourth valid alternative regression model relates to a novel Tucker-rank estimation approach using robust minimum description length MDL, published by Yokota et al. in 2017 titled: Robust Multilinear Tensor Rank Estimation Using Higher Order Singular Value Decomposition and Information Criteria, incorporated by reference for explaining the estimation approach using MDL, incorporated by reference for explaining the estimation approach using robust minimum description length MDL.

A fifth valid alternative regression model relates to a multilinear Tensor Rank Estimation based on L1-regularized orthogonal CP decomposition TREL1, published by Shi et al. in 2017 titled: Tensor Rank Estimation and Completion via CP-based Nuclear Norm, incorporated by reference for explaining multilinear Tensor Rank Estimation based on L1-regularized orthogonal CP decomposition TREL1. Using a block coordinate descent approach, the CP components and corresponding weight vectors are iteratively updated. Finally, TREL1 automatically determines the MTR by pruning the zero entries of the weight vector.

The BTTR remains the preferred regression model because the above mentioned alternative multiway regression models are all computationally demanding as their model parameters are optimized via time consuming techniques such as cross-validation on a sufficient set of parameter combinations. BTTR is tackling this issue efficiently.

Preferably, the BCI further comprising an ECoG signal feature decoder connected to said output to decode the simulated ECoG signal features. An ECoG signal feature decoder is typically embodied by a Deep Learning Network that generates a compressed vocoder representation, which in turn may be decompressed and fed into a vocoder that synthesizes an audio signal. Preferably, the BCI is operationally connected to a vocoder located downstream of the decoder to transform the decoded ECoG signal features into speech.

The invention further relates to a method for processing brain activity at a brain computer interface BCI, the method comprising the steps:
- receiving EEG signals, the EEG signals being captured by at least one electroencephalography EEG sensor;
- running an associative model applying a multiway regression approach trained to simulate electrocorticography ECoG signal features from EEG signals received; and
- transmitting the simulated ECoG signal features The effects and advantages described above in relation to the BCI of the invention are equally or analogue for the method of the invention.

Further advantageous embodiments and features of the present invention are subject of dependent claims and will be described hereunder in the detailed description.

The invention will now be described in more details with respect to the drawings illustrating some preferred embodiments of the invention. In the drawings:

FIG. 4 illustrates a BTTR scheme usable in the associative model used in the invention;

FIG. 7 illustrates a more detailed embodiment of the associative model.

In the drawings a same reference number has been allocated to a same or analogous element.

Figure 1:
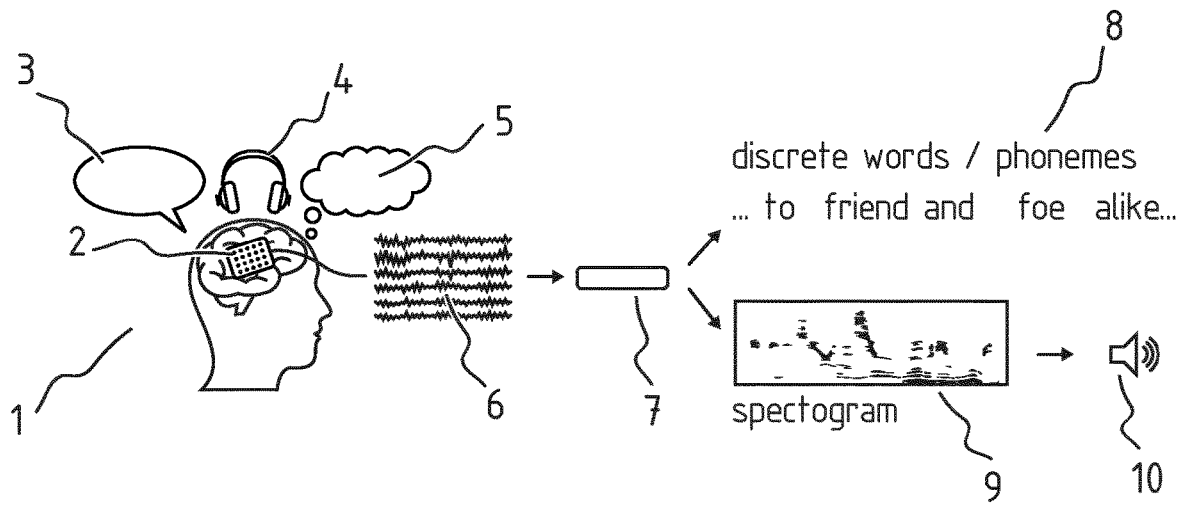
FIG. 1 illustrates a combination of individually known techniques.

FIG. 1 illustrates a human 1. Human communication has different aspects, all controlled by the human brain. An important aspect of human communication is speech. Brain activity relating to speech has been the subject of research and developments for many years. Aspects of the invention are based on an insight that brain activity relating to speech can be subdivided into three main categories: performed speech 3, perceived speech 4 and imagined speech 5. Other minor categories include mimed speech, which is non-vocalized speech.

FIG. 1 illustrates a general set-up of a speech BCI, from electrode to speech transcription or sound vocalization. While a subject 1 utters 3, hears 4, or imagines uttering 5 a word or sentence, his/her brain signals are recorded by an ECoG sensor 2. The ECoG sensor outputs ECoG signals 6, which are analyzed to extract signal features and fed into a decoder 7 that either predicts intended speech, illustrated as spectrogram 9, also referred to as continuous decoding, or illustrated as discrete words, phonemes, etc. 8, also referred to as discrete decoding. The shown BCI operates on electrocorticography ECoG signals 6 recorded from an electrode grid 2 placed on the surface of brain regions involved in speech processing. Given the fast-changing dynamics of speech, only recording techniques with high temporal bandwidth have proven, using prior art decoding techniques, to be appropriate.

Multiple ECoG signal decoders have been developed for both continuous decoding and discrete decoding. Aspects of the invention aim at reusing the decoders that have been developed. Because ECoG sensors require a craniotomy, other sensors for example EEG sensors are preferred.

In the context of this description, a signal refers to the amplitude changing over time whereas a signal feature is a characteristic of a signal, e.g. the average amplitude, range, frequency, envelope, . . . . Therefore ECoG signal and ECoG feature is not the same. Likewise, EEG signal and EEG feature is not the same.

Figure 2:
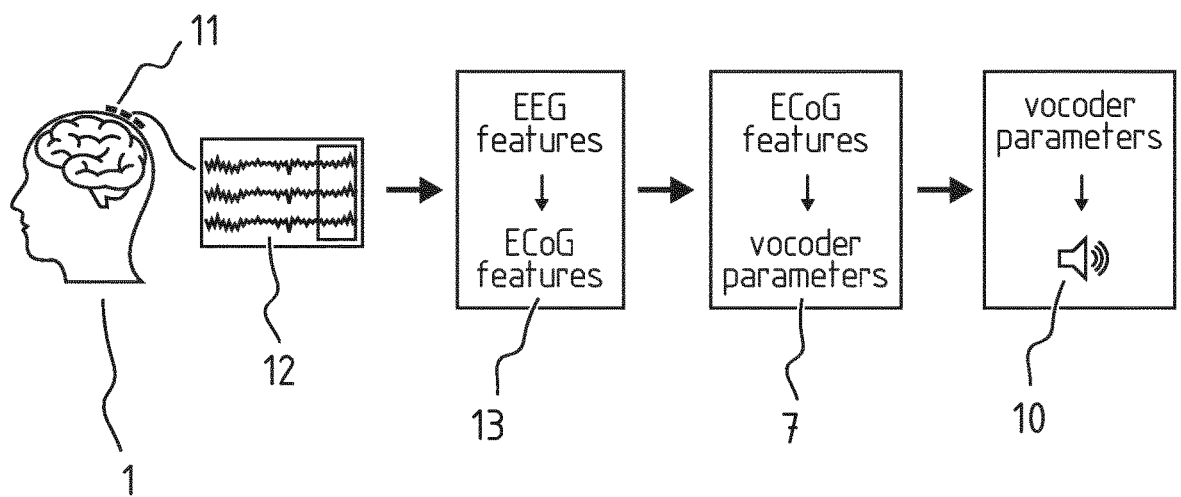
FIG. 2 illustrates a first embodiment of the invention.

FIG. 2 illustrates an aspect of the invention wherein a BCI running an associative model 13, also called associator. The associative model 13 is trained to simulate ECoG signal features from EEG signals. Therefore an EEG sensor 11 is placed and positioned on a human subject 1. This EEG sensor 11 generates EEG signals 12 which are input into the BCI. Based on these EEG signals 12, the associator 13 determines ECoG signal features. These ECoG signal features are fed into a decoder 7. Since the signal features fed into the decoder 7 are ECoG signal features, a prior art decoder 7 can be reused. The decoder 7 can be connected to a speaker for synthetization and outputting of the decoded speech. As an alternative, the decoder 7 is connected to a screen for visualizing the decoded speech. Further alternative, the decoder 7 is connected to a memory for recording the decoded speech. The principles and mechanisms used to embody the associator 13 are described in more detail and in relation to some examples hereunder.

Figure 3:
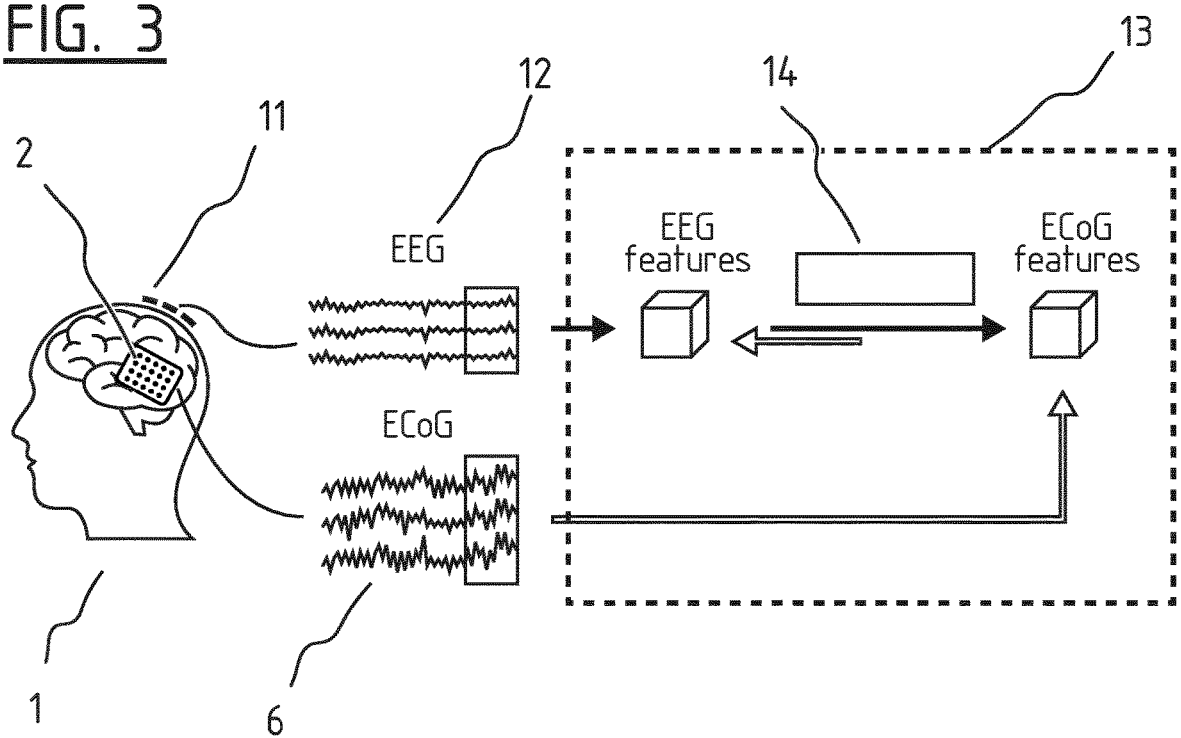
FIG. 3 illustrates an aspect related to training and application of the associative model used in the invention.

FIG. 3 illustrates an aspect of the invention wherein the associative model 13 is trained. The associator 13 is embodied as a regression model to predict ECoG signal features from EEG signals, thus, despite the more limited frequency band of EEG. The skilled person will know that EEG records only low frequencies being frequencies below the low gamma band. However, via the regression model, low gamma ECoG can be predicted from low frequency ECoG. Furthermore, also high gamma can be predicted. Therefore, using the regression model, both low and high ECoG frequency features are predictable from EEG signals. The open arrows in FIG. 3 in the associator 13 represent signal flows that will only flow in a training situation. The closed arrows in FIG. 3 in the associator 13 represent signal flows that will flow both in a training and in an operational situation. Reference number 14 refers to a regression model which is used in the associator 13, preferably embodied as a BTTR, that is further explained hereunder.

The training stage comprises three substages, each focusing and training the model on a particular type of speech. Different training substages are conducted for different types of speech. A first training substage is conducted for performed speech 3, a second training substage is conducted for perceived speech 4 and a third training substage is conducted for imagined speech 5. The term first, second and third in this context do not relate to a sequence or order of performing these training substages, but is only used to make a clear distinction between different training substages. The skilled person may develop a training program wherein each substage is individually conducted or wherein predetermined combinations of substages are conducted in such a manner that a distinction in predicting performed speech 3, perceived speech 4 and imagined speech 5 is made. Tests have shown that not only a distinction can be detected in brain recordings, but also an overlap is clearly detectable. This is due to the fact that in the human brain, for example, performed speech 3 is not completely separately represented from imagined speech, on the contrary. This creates overlaps in brain activity that can be observed when recording ECoG signals. By being aware of the type of speech that is recorded, as a result of training in different substages, knowledge of these overlaps in brain activity is usable to further enhance the decoding and to enhance the prediction of ECoG signals from EEG signals.

Figure 4:
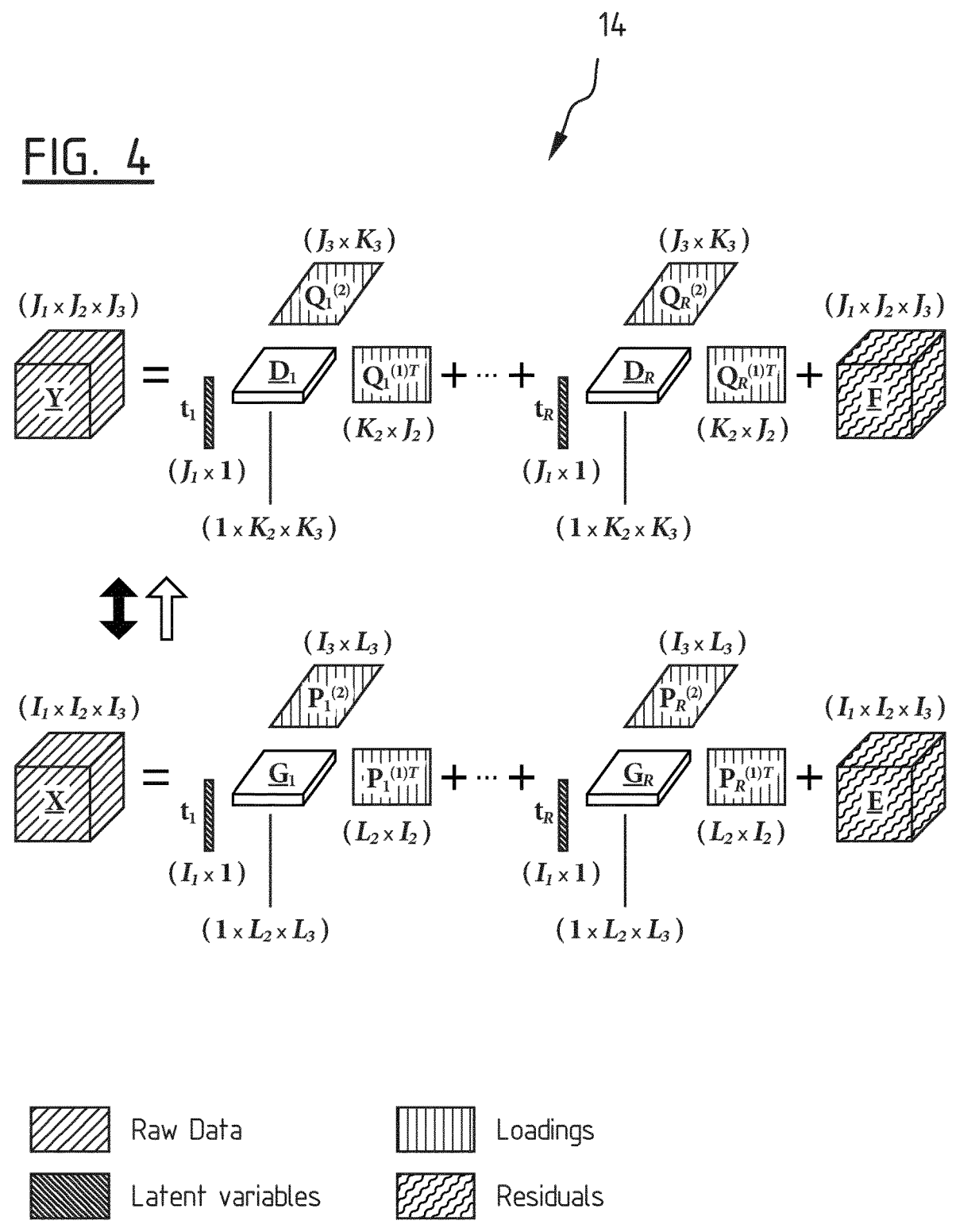

FIG. 4 illustrates a scheme of the block term tensor regression BTTR 14 adopted as associative model in the associator 13 for the prediction of ECoG signal features from EEG signals. In the design, EEG and ECoG recordings are configured as 4th-order tensors $\underline{X}$ and $\underline{Y}$, however in FIG. 4, for visualization purposes, only $\overline{3}$ dimensions are shown. The model is first trained on jointly recorded EEG/ECoG signals. In a second stage, also called the operational stage, the model is applied to EEG signals to predict ECoG signal features. The double, closed, arrow indicates the information flow during training, the single, open, upwardly directed arrow indicates the information flow during the operational stage or during prediction or simulation. The decomposition of each block into loading matrices of certain dimensionality and into core tensors $\underline{G}$ and $\underline{D}$ as well as the number of those blocks, deflation-based approach, are preferably automatically determined.

In an experiment in Belgium, a male patient was recruited that suffered from drug-resistant epilepsy. To locate the epileptogenic region, the patient was implanted with a subdural ECoG grid of 6×8 platinum electrodes embedded in silastic covering the precentral gyrus and the superior and middle frontal gyri of the right hemisphere. The electrode positions were extracted from the pre-implant MRI and post-implant CT scans, using a known procedure. ECoG signals were continuously recorded at 256 Hz. During the clinical workup phase the patient volunteered to participate in several experiments. The experiments were structured into a series of steps being an instruction, a pause, and task performance. The focus of the experiment was to show the potential of tensor-based techniques to regress ECoG signals across frequency bands.

In the conducted experiment, raw ECoG signals were re-referenced to the common average reference (CAR) of all subdural channels, and the powerline interference removed using a 4th order Butterworth notch filter between 49 and 51 Hz. Next, 3-second epochs were cut from the continuous signals, locked to the offset of the instruction but before the task, further referred to as 'baseline epochs', 60 in total. Finally, for each baseline epoch, the activity in 6 frequency bands was extracted using 4th order Butterworth bandpass filters: δ (0.1-1 Hz, 1-4 Hz), θ (4-8 Hz), α (8-12 Hz), β1 (12-24 Hz), β2 (24-34 Hz) and the low gamma band (34-70 Hz).

In order to reconstruct low gamma activity from the five other frequency bands, a Block-Term Tensor Regression BTTR is used, which utilizes a deflation-based approach to iteratively model the relationship between the predictor and the response as a series of blocks, as illustrated in FIG. 4. Details regarding the BTTR are described in F Camarrone: Multiway decoding of finger movements from intracranial brain signals, translating thoughts into finger control, which is incorporated herein by reference for explaining the BTTR. Further details regarding the BTTR are described in Bob Van Dyck: Predicting low gamma—from lower frequency band activity in electrocorticography, which is also incorporated herein by reference for explaining the BTTR. Given a set of multiway data $\underline{X}$train RI1× . . . ×IN and a vectorial response $y_{train}$ RI1×1, BTTR training consists of automatically identifying K blocks:

$$\underline{X}_{train} = \sum_{k=1}^{K} \underline{G}_k \times t_k \times P_k^{(2)} \times \ldots \times P_k^{(N)} + \underline{E}_k \text{ and}$$

$$y_{train} = \sum_{k=1}^{K} u_k + f_k \text{ with } u_k = t_k b_k,$$

During training, the core tensor for the k-th block (G), the k-th loading matrix for the n-th mode (P) and the regression coefficient ($b_k$) are computed so that the model's final prediction is as follows:

$$y_{test} = \text{Tb} = \underline{X}_{test} \text{Wb}$$

The BTTR algorithm thus computes a set of latent variables such that each block of the multiway predictor variable is maximally correlated with the corresponding block of the vectorial response variable. The dimensions of $t_k$ and $P_k^{(n)}$ are automatically determined using Automatic Component Extraction ACE and/or its improved version augmented with automatic latent component selection, called Automatic Correlated Component Selection ACCoS. The only model parameter left undetermined thus is K, the upper limit of the deflation scheme. It is preferred to determine K via a cross-validation procedure.

The BTTR algorithm was used to predict the low gamma (40-70 Hz) band signal from the corresponding lower frequency signal in the case of baseline ECoG recordings. The experiment shows that the low gamma signal is predicted rather well except perhaps for extremal and small amplitudes, determined according to Pearson's correlation as is described above. Importantly, the phase is preserved which is important as gamma oscillations are thought to be our best candidate to unravel the role of aggregate electrical activity in predicting synchronized spiking of individual neurons. The above is based on the insight that the predictability of low gamma signals, in amplitude and phase, from low frequency activity, is due to ECoG signals being broadband modulated.

Figure 5:
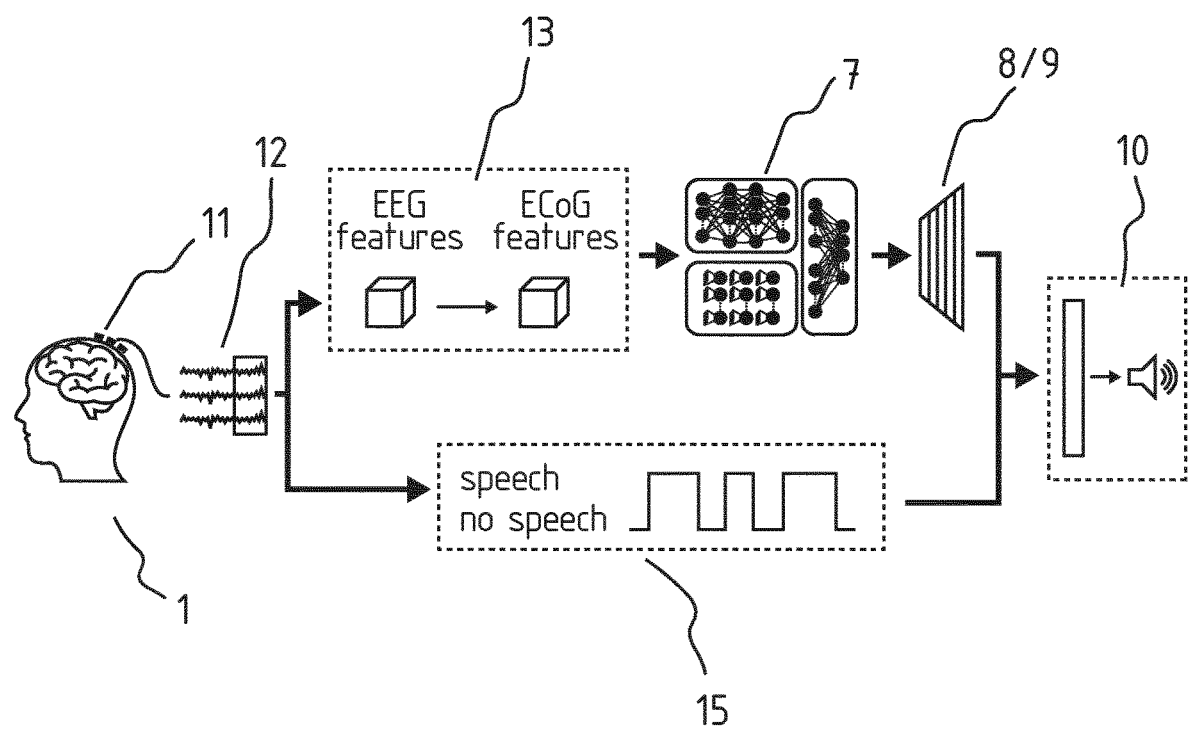
FIG. 5 illustrates a second embodiment of the invention.

FIG. 5 shows another embodiment of the invention. FIG. 5 shows how a human subject 1 is provided with EEG sensors 11. The EEG signals 12, produced by the EEG sensors 11, are fed into the BCI. In the BCI, the associator 13 determines ECoG signal features which are decoded in a decoder 7. The decoded signals can be decompressed and/or classified into discrete words 8 (not shown in FIG. 5) or can be decompressed into a spectrogram 9 to be fed to a vocoder and speaker 10. In parallel, a brain switch is used to detect when the user wants to generate speech. In particular, the brain switch 15 detects whether the user wants to perform speech. In other words, the brain switch distinguishes between inner speech and performed speech. The speaker is switched on and off via this brain switch to avoid erroneous audio signals or false positives.

Figure 6:
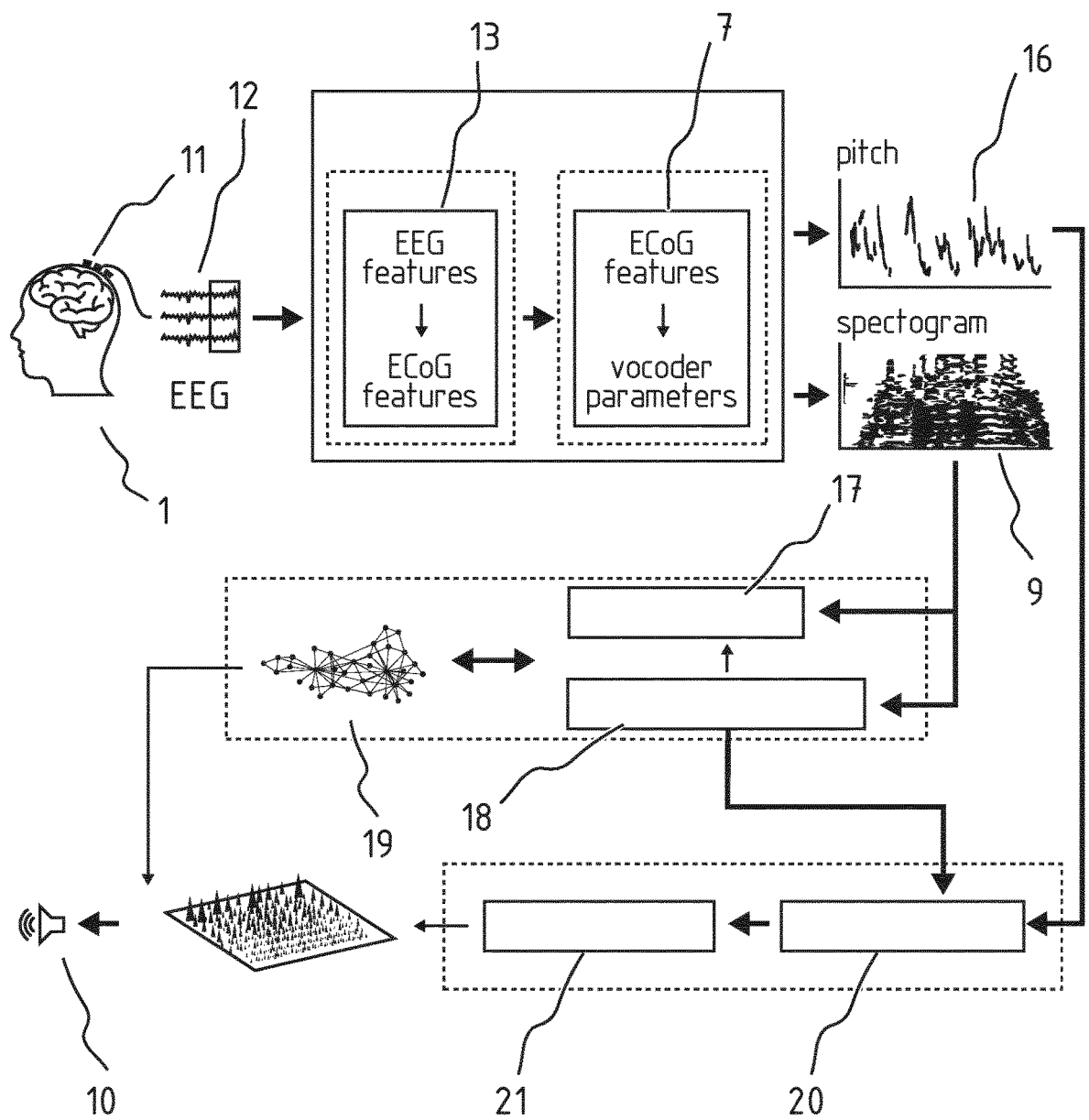
FIG. 6 illustrates a third embodiment of the invention.

Using prior art techniques, EEG-based speech decoding never went beyond discerning a few syllables or the envelope of the perceived acoustic signal. FIG. 6 illustrates a further embodiment that is usable as a fallback solution, when detailed speech cannot directly be retrieved from the EEG recordings. In the embodiment of FIG. 6, a semantic net 19 is used to select words with matching phonetics and/or prosodics 18, and emotional states 17. In this way word sequences can be identified and, via a language model 21, be output to a speaker 10. Furthermore, the subject's expression type 20 can be deduced from the speech recordings to further shape the output form of the sound. The mechanism above forms a spoken language model that enables to give the intended expression to a word sequence selected from a 'bag of words' with a similar phonetic structure. In the embodiment of FIG. 6, additionally to the spectrogram 9 being determined by the decoder, also a pitch 16 is determined.

FIG. 7 shows a more detailed embodiment of how an associator 13 may be structured and how the associator model is trained. In the figure, the open arrows represent signal flows that will only flow in a training situation. The closed arrows represent signal flows that will flow both in a training and in an operational situation. The figure shows that multiple models are used to calculate or transform signals. In step 22 EEG features are extracted from EEG signals 12. For this step 22, known procedures, e.g. frequency analysis can be used. A first model 23 determines ECoG features from EEG features. The first model 23 is preferably embodied as an above-described BTTR. Alternatively, the first model 23 simply copies the EEG features into low band ECoG features. In step 24 ECoG features are extracted from ECoG signals 6. A second model 25 determines ECoG high gamma features from ECoG low band features. The second model 25 is embodied as an above-described BTTR. A third model 26 determines ECoG low gamma features from ECoG low band features. The third model 26 is embodied as an above-described BTTR. In step 27 the low band features are merged with the low gamma features and high gamma features to aggregate the ECoG signal features that can be further decoded.

The present inventions may be embodied in other specific apparatus and/or methods. The described embodiments are to be considered in all respects as only illustrative and not restrictive. In particular, the scope of the invention is indicated by the appended claims rather than by the description and figures herein. All changes that come within the meaning and range of equivalency of the claims are to be embraced within their scope.

A person of skill in the art would readily recognize that steps of various above-described methods can be performed by programmed computers. Herein, some embodiments are also intended to cover program storage devices, e.g., digital data storage media, which are machine or computer readable and encode machine-executable or computer-executable programs of instructions, wherein said instructions perform some or all of the steps of said above-described methods. The program storage devices may be, e.g., digital memories, magnetic storage media such as a magnetic disks and magnetic tapes, hard drives, or optically readable digital data storage media. The embodiments are also intended to cover computers programmed to perform said steps of the above-described methods.

The description and drawings merely illustrate the principles of the invention. It will thus be appreciated that those skilled in the art will be able to devise various arrangements that, although not explicitly described or shown herein, embody the principles of the invention and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

The functions of the various elements shown in the figures, including any functional blocks labeled as "processors", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

The invention claimed is:

1. Brain computer interface ("BCI") comprising an input connected to at least one electroencephalography ("EEG") sensor and receiving EEG signals generated by the at least one EEG sensor, the BCI further comprising a processor running an associative model applying a multiway regression approach trained to simulate electrocorticography ("ECOG") signal features from the received EEG signals, the BCI comprising an output to transmit the simulated ECOG signal features.

2. The BCI according to claim 1, wherein the processor running the associative model is configured to operate in two stages, wherein
   in a first stage of the two stages, features in a first frequency band of a simulated ECOG signal are simulated based on the received EEG signals, wherein the first frequency band corresponds to a frequency band of the received EEG signals, wherein the simulated ECoG signal is simulated based on the received EEG signals;
   in a second stage of the two stages, features in a frequency band of the simulated ECOG signal with the highest frequency are simulated based on the received EEG signals.

3. The BCI according to claim 2, wherein in the second stage a frequency band of the simulated ECOG signal with the highest frequency is simulated based on the received EEG signals indirectly based on the first stage features in the first frequency band of the simulated ECOG signal.

4. The BCI according to claim 2, wherein the frequency band of the simulated ECoG signal with the highest frequency comprises a low gamma sub-band and a high gamma sub-band and wherein processor is further configured, in the second stage, to separately perform feature simulation in a low gamma sub-band and in a high gamma sub-band.

5. The BCI according to claim 1, wherein the processor running the associative model comprises a training state and an operational state, wherein at least in the training state, the BCI comprises a further input connected to at least one ECoG sensor and receiving ECOG signals generated by the at least one ECoG sensor such that via the input and the further input, the received EEG signals and the received ECOG signals can be simultaneously received, and wherein the processor is adapted to train the associative model by feeding the associative model with the simultaneously received EEG and ECOG signals.

6. The BCI according to claim 5, wherein the training state comprises three training stages, a first training stage of the three training stages relating to perceived speech, a second training stage of the three training stages relating to performed speech, a third training stage of the three training stages relating to inner speech, the received EEG signals being fed into the associative model at least for each of these stages separately.

7. The BCI according to claim 1, wherein the associative model comprises a block term tensor regression BTTR scheme.

8. The BCI according to claim 1, further comprising an ECOG signal feature decoder connected to said output to decode the simulated ECOG signal features.

9. The BCI according to claim 8, operationally connected to a vocoder located downstream of the decoder to transform the decoded ECOG signal features into speech.

10. A method for processing brain activity, the method comprising the steps:
   receiving electroencephalography ("EEG") signals via an input of a brain computer interface ("BCI"), the EEG signals being generated by at least one EEG sensor connected to the input;
   running an associative model applying a multiway regression approach trained to simulate electrocorticography ("ECOG") signal features from the received EEG signals via a processor of the BCI; and
   transmitting the simulated ECOG signal features via an output of the BCI.

11. The method according to claim 10, wherein the step of running the associative model comprises a training state and an operational state, wherein at least in the training state, the BCI comprises a further input connected to at least one ECoG sensor and receiving ECOG signals generated by the at least one ECoG sensor such that via the input and the further input, the received EEG signals and the received ECOG signals can be simultaneously received, and wherein the method comprises training the associative model by feeding the model with the simultaneously received EEG and ECOG signals.

12. The method according to claim 11, wherein the step of training the associative model comprises:
   training the associative model with first signals relating to perceived speech;
   training the associative model with second signals relating to performed speech; and
   training the associative model with third signals relating to inner speech; and
   wherein the first, second and third signals are fed into the model separately.

* * * * *